US008211679B2

(12) United States Patent
Datta et al.

(10) Patent No.: US 8,211,679 B2
(45) Date of Patent: Jul. 3, 2012

(54) PROCESS FOR PRODUCING ETHANOL

(75) Inventors: Rathin Datta, Chicago, IL (US); Rahul Basu, Naperville, IL (US); Hans E. Grethlein, Syracuse, NY (US); Richard W. Baker, Palo Alto, CA (US); Yu Huang, Palo Alto, CA (US)

(73) Assignee: Coskata, Inc., Warrenville, IL (US)

( * ) Notice: Subject to any disclaimer, the term of this patent is extended or adjusted under 35 U.S.C. 154(b) by 1058 days.

(21) Appl. No.: 12/036,859

(22) Filed: Feb. 25, 2008

(65) Prior Publication Data

US 2009/0215139 A1 Aug. 27, 2009

(51) Int. Cl.
*C12P 7/14* (2006.01)
(52) U.S. Cl. .......................... 435/162; 435/7.1
(58) Field of Classification Search .................. None
See application file for complete search history.

(56) References Cited

U.S. PATENT DOCUMENTS

| | | | |
|---|---|---|---|
| 4,336,335 A | | 6/1982 | Muller et al. |
| 4,777,135 A | * | 10/1988 | Husted et al. ................ 435/160 |
| 4,778,688 A | | 10/1988 | Matson |
| 4,900,402 A | | 2/1990 | Kaschemekat et al. |
| 5,173,429 A | | 12/1992 | Gaddy et al. |
| 6,136,577 A | | 10/2000 | Gaddy |
| 6,340,581 B1 | | 1/2002 | Gaddy |
| 6,755,975 B2 | | 6/2004 | Vane et al. |
| 6,899,743 B2 | | 5/2005 | Wijmans et al. |
| 6,919,488 B2 | | 7/2005 | Melnichuk et al. |
| 7,118,672 B2 | | 10/2006 | Husain et al. |
| 7,285,402 B2 | | 10/2007 | Gaddy et al. |
| 2006/0163157 A1 | | 7/2006 | Cote et al. |
| 2007/0275447 A1 | | 11/2007 | Lewis et al. |
| 2008/0057554 A1 | | 3/2008 | Huhnke et al. |
| 2008/0305539 A1 | | 12/2008 | Hickey et al. |
| 2008/0305540 A1 | | 12/2008 | Hickey et al. |
| 2009/0029434 A1 | | 1/2009 | Tsai et al. |
| 2009/0035848 A1 | | 2/2009 | Hickey et al. |
| 2009/0104676 A1 | | 4/2009 | Tsai et al. |
| 2009/0215142 A1 | | 8/2009 | Tsai et al. |
| 2009/0215153 A1 | | 8/2009 | Tsai et al. |
| 2009/0215163 A1 | | 8/2009 | Tsai et al. |
| 2009/0286296 A1 | | 11/2009 | Hickey et al. |

FOREIGN PATENT DOCUMENTS

| | | |
|---|---|---|
| JP | 06-063303 A | 3/1994 |
| JP | 06-063303 | 3/2006 |
| WO | WO2008154301 | 12/2008 |

OTHER PUBLICATIONS

Guerry et al. "General Method for the Isolation of Plasmid Deoxyribonucleic Acid" Journal of Bacteriology, Nov. 1973, p. 1064-1066.*
O'Brien et al. (Appl. Microbiol Biotechnol. 1996, vol. 44, pp. 699-704).*
Shabtai et al. (Biotechnol and Bioengin., vol. 38, pp. 869-879, 1991).*
Groot et al.(Bioprocess Engin., 1992, vol. 8, pp. 99-111).*
Leeper et al. (J. of Membrane Science, vol. 30, pp. 289-312, 1987).*
O'Brien et al. (J. of Membrane Science, vol. 166, 2000, pp. 105-111).*
Mori et al. (Biotechnol and Bioeng., vol. 36, pp. 849-853, 1990).*
U.S. Appl. No. 12/258,193, filed Oct. 24, 2008, 2008, Datta et al.
Clausen, E.C., et al., "Ethanol From Biomass by Gasification/Fermentation", Presented at Plastics, Tires, Auto Wastes/Biomass MSW Symposium, Fall 1993, Chicago, 38 (3).
Klasson, K.T., et al., "Biological Production of Liquid and Gaseous Fuels from Synthesis Gas," Appl. Biochem. Biotechnol., vol. 24-25, No. 1, Mar. 1990, 857-873.
Vega, J. L., et al., "The Biological Production of Ethanol from Synthesis Gas," Appl. Biochem. Biotechnol. vol. 20-21, No. 1, Jan. 1989, 781-797.
Phillips, John R., et al., "Synthesis Gas as Substrate for the Biological Production of Fuels and Chemicals," Appl. Biochem. Biotechnol. vol. 45-46, No. 1, Mar. 1994, 145-157.
Barik, S., et al., "Biological Production of Alcohols from Coal Through Indirect Liquefaction," Appl. Biochem. Biotechnol. vol. 18, No. 1, Aug. 1988, 363-387.
Henstra, A. et al., "Microbiology of synthesis gas fermentation for biofuel production," Current Opinion in Biotechnol., vol. 18, Mar. 2007, 200-206.
Abrini, J. et al., "*Clostridium autoethanogenum*, sp. nov., an anaerobic bacterium that produces ethanol from carbon monoxide," Arch. Microbiol. vol. 161, 1994, 345-351.
Das, A. and Ljungdahl, L.G., "Electron Transport System in Acetogens," Biochemistry and Physiology of Anaerobic Bacteria, 2003, 191-204, Springer-Verlag New York, Inc., New York, US.
Drake, H. and Kusel, K., "How the Diverse Physiologic Potentials of Acetogens Determine Their In Situ Realities," Biochemistry and Physiology of Anaerobic Bacteria, 2003, 171-190, Springer-Verlag New York, Inc., New York, US.
Grethlein, A. et al., "Evidence for Production of n-Butanol from Carbon Monoxide by Butyribacterium methylotrophicum," J. Ferment. Bioeng., vol. 72, No. 1, 1991, 58-60.
Worden, R.M., et al., "Production of butanol and ethanol from synthesis gas via fermentation," Fuel. vol. 70, May 1991, 615-619.

* cited by examiner

*Primary Examiner* — Hope Robinson
(74) *Attorney, Agent, or Firm* — Cardinal Law Group

(57) ABSTRACT

Ethanol and other liquid products produced by contacting carbon monoxide (CO) and/or a mixture of $CO_2$ (carbon dioxide) and $H_2$ (hydrogen) with a microorganism in a bioreactor are separated using a combination of distillation and vapor permeation membranes. The bioreactor passes an effluent with an ethanol concentration of 1 to 6 wt % to a distillation column that produces an overhead vapor stream enriched in ethanol. A series of vapor permeation membranes retain ethanol as retentate and produce a 99 wt % or higher ethanol product. Ethanol depleted permeate streams flow back to the column and the bioreactor. Coupling a bioreactor with distillation and pervaporation efficiently and economically separates ethanol when present at low concentration in an aqueous fermentation broth. The separation arrangement may also include a flash zone ahead of the distillation column to raise the concentration of the ethanol in the input stream to the distillation column.

20 Claims, 2 Drawing Sheets

PROCESS FOR PRODUCING ETHANOL

FIELD OF THE INVENTION

This invention relates to the biological conversion of CO and mixtures of $CO_2$ and $H_2$ to liquid products and the recovery of ethanol from the effluent stream of such conversions.

DETAILED DESCRIPTION

Background

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). These processes ordinarily use the readily fermentable carbohydrates in relatively high concentration so that the resulting fermentation liquid readily achieves an ethanol concentration of at least 7% and routinely achieves ethanol concentrations of more than 10%.

The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers). For example, breaking down these recalcitrant structures to provide fermentable sugars for bioconversion to ethanol typically requires pretreatment steps together with chemical/enzymatic hydrolysis. Furthermore, conventional yeasts are unable to ferment the $C_5$ sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$ and $CO_2$ with other components such as $CH_4$, $N_2$, $NH_3$, $H_2S$ and other trace gases) and then ferment this gas with anaerobic microorganisms to produce biofuels such as ethanol, n-butanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas can be made from many other carbonaceous feedstocks such as natural gas, reformed gas, peat, petroleum coke, coal, solid waste and land fill gas, making this a more universal technology path.

However, this technology path requires that the syngas components CO and $H_2$ be efficiently and economically dissolved in the aqueous medium and transferred to anaerobic microorganisms that convert them to the desired products. And very large quantities of these gases are required. For example, the theoretical equations for CO or $H_2$ to ethanol are:

$$6CO + 3H_2O \rightarrow C_2H_5OH + 4CO_2$$

$$6H_2 + 2CO_2 \rightarrow C_2H_5OH + 3H_2O$$

Thus 6 moles of relatively insoluble gases such as CO or $H_2$ have to transfer to an aqueous medium for each mole of ethanol. Other products such as acetic acid and n-butanol have similar large stoichiometric requirements for the gases. Furthermore, the anaerobic microorganisms that bring about these bioconversions generate very little metabolic energy from these bioconversions. Consequently they grow very slowly and often continue the conversions during the non-growth phase of their life cycle to gain metabolic energy for their maintenance.

Many devices and equipment are used for gas transfer to micro organisms in fermentation and waste treatment applications. Most of these reactors or systems are configured for use with micro organisms in planktonic form i.e. they exist as individual cells in liquid medium. Furthermore, to get high yields and production rates the cell concentrations in the bioreactor need to be high and this requires some form of cell recycle or retention. Conventionally, this is achieved by filtration of the fermentation broth through microporous or nonporous membranes, returning the cells and purging the excess. These systems are expensive and require extensive maintenance and cleaning of the membranes to maintain the fluxes and other performance parameters.

Cell retention by formation of biofilms is a very good and often inexpensive way to increase the density of micro organisms in bioreactors. This requires a solid matrix with large surface area for the cells to colonize and form a biofilm that contains the metabolizing cells in a matrix of biopolymers that the cells generate. Trickle bed and some fluidized bed bioreactors make use of biofilms to retain microbial cells on solid surfaces while providing dissolved gases in the liquid by flow past the solid matrix. They suffer from either being very large or unable to provide sufficient gas dissolution rates.

The use of bioreactors that retain biofilms has been proposed for the production of liquid fuels. U.S. Ser. No. 11/781,717 (filed Jul. 23, 2007) shows the use of a bioreactor to support microorganisms on a membrane (preferably hollow fiber membranes) for the production of ethanol from syngas. U.S. Ser. No. 11/833,864 (filed Aug. 3, 2007) shows the use of bioreactor for producing ethanol from syngas using microorganisms retained on media that circulates as a moving bed in a fermentation broth. In both of these bioreactors the fermentation broth retains the ethanol from the microorganisms in dilute concentration.

All these systems for conversion of biomass derived syngas rely on a fermentation broth that provides a low concentration of ethanol in a relatively large volume of aqueous liquid. Ethanol concentration will ordinarily fall below 6% and in most cases less than 4%. As a result practical recovery of ethanol from the fermentation broth requires a separation system that can efficiently recover the ethanol from the dilute fermentation broth.

In addition to low concentrations of ethanol, the fermentation liquid as with any biological process will contain other dissolved and undissolved components. Such components include cells, proteins, salts, unfermented solubles and colloidal materials. These materials can impose impurities into the separation processes thereby imposing additional challenges to efficient and economical ethanol recovery.

U.S. Pat. No. 6,899,743 B2 and U.S. Pat. No. 6,755,975 B2 disclose processes for recovering organic compounds such as ethanol from water by the use of pervaporation followed by dephlegmation. These patents describe the separation of organic mixtures with concentrations as low as 1% but do not provide any solution to the problem of impurities or undissolved materials.

Practical production of ethanol from biomass requires the effective coupling of four different zones. First a gasification zone that converts biomass into syngas, defined to mean at least one of CO or a mixture of $CO_2$ and $H_2$. Next a fermentation zone, preferably in the form of a bioreactor, receives the syngas feed and delivers it to the microorganisms that expel ethanol into a liquid broth. Finally a separation zone must recover ethanol from the broth in an energy efficient manner.

SUMMARY OF THE INVENTION

It has been found the coupling of a bioreactor with a separation zone that uses stripping or distillation followed by vapor phase permeation can efficiently and economically separate ethanol when present at low concentration in an aqueous fermentation broth. Having a system of practical ethanol recovery in such low concentrations is essential to utilizing syngas generated from biomass. Biomass provides an extensive and renewable source for the generation of syngas and the ultimate production of ethanol. The system may benefit from using a separation zone that operates as a vacuum stripping or distillation column.

A gasifier will ordinarily produce the syngas from biomass in the form of wood, switchgrass, corn stover and other waste materials. The biomass is dried to around 20% moisture and gasified either by air, enriched oxygen or pure oxygen to produce a syngas that is a typical mixture of CO, H2 and CO2 with other components such a CH4, N2 and other trace gases and impurities. The CO and H2/CO2 are converted to ethanol in the bioreactor.

In one form of this invention a feed gas containing CO or a mixture of $CO_2$ and $H_2$ contacts a microorganism in a bioreactor. The microorganism metabolizes the feed gas to produce an aqueous ethanol effluent having an ethanol concentration of less that 6 wt %. A portion of the ethanol effluent returns to the bioreactor as a broth fraction. Another portion of the ethanol effluent passes as a dilute ethanol stream to a stripping column. The stripping column separates the dilute ethanol stream into an ethanol depleted bottoms stream and an overhead vapor stream enriched in ethanol and preferably containing at least 30 wt % ethanol. At least a portion of the ethanol depleted bottoms stream and at least a portion of the broth fraction return to the bioreactor. Compression of the overhead vapor stream to at least 2 atmospheres provides a compressed vapor stream. At least a portion of the compressed vapor stream contacts a membrane in a first vapor permeation unit to produce a first permeate stream with an ethanol concentration of at least 2 wt % and a retentate having at least 80 wt % ethanol. At least a portion of the first vapor permeate stream returns to the stripping column. The retentate enters a second permeation unit and contacts a membrane to produce a dehydrated ethanol stream having at least 99.0 wt % ethanol and a second permeate stream. At least a portion of the second permeate stream returns to the stripping column and an ethanol product is recovered from the dehydrated ethanol stream.

The integration of the distillation column with the low ethanol concentration effluent brings numerous advantages to the operation and efficiency of the process arrangement. The distillation column enables efficient ethanol recovery with a fermentation broth having ethanol concentrations as low as 1%. There is an important need for a way to efficiently recover ethanol from such fermentation broths given the low ethanol tolerance of the anaerobic bacteria that are suitable for biomass derived feed gas. This separation arrangement succeeds in taking the fermentation broth with ethanol as low as 1 to 4% and generating an ethanol overhead from the distillation column of over 30% and as high as 50%. The stripping function of the distillation column together with the large volume of liquid coming from the column bottoms minimizes or eliminates fouling problems of the membranes by protecting them from bacterial cells and other non-volatile impurities of the fermentation broth. When the distillation is conducted under vacuum, the bottoms do not require high temperatures that result in the formation of toxic by-products. Thus, the majority of the column bottoms can return directly to the bioreactor. This return enables a conservation of water and the uptake of acetic acid and/or butyric acid that the anaerobic bacteria can convert to more ethanol in the bioreactor. A small fraction of the column bottoms undergoes purging of acetates and other insolubles via an anaerobic digestor that converts these materials to methane. Recovered methane gas can provide a further source of process energy. For example the methane can be used as an energy source in the gasification step.

Further advantages derive from the limited number of phase changes from the low operating temperatures of a vacuum distillation column and the downstream processing of the ethanol overhead in the permeation units. Operation of a vacuum distillation column at moderate temperatures reduces the need for reflux over conventional columns and minimizes the vapor-liquid phase changes. In fact, when the concentration of ethanol in the effluent from the bioreactor exceeds 3 wt %, the process can operate without recycle of any distillation column overhead. Furthermore, the vapor permeation units operate at high efficiency since there are no phase changes. The first permeation unit provides vapor for the distillation column in the form of a water rich permeate. The compression energy associated with the latent heat of vaporization of the dehydrated ethanol product is also recovered via heat exchange with the column bottoms.

Another form of this invention may incorporate a flash zone between the bioreactor and the distillation column. The low concentration of the ethanol stream to which this invention applies makes a flash step particularly useful. Since the alcohol concentration at typical equilibrium conditions is 9 to 12 times greater in the vapor phase than in the liquid phase the flash step can improve separation efficiency. The flash step can provide a highly efficient enrichment of the ethanol containing stream before it enters the distillation column. The flash zone provides the most benefit at lower concentrations of ethanol in the dilute ethanol stream. Even small reductions in the pressure of the broth can achieve useful flash ratios.

The particular configuration of the flash zone and its specific integration into the bioreactor and recovery system may take many forms. The flash zone may receive all or only a portion of the fermentation broth that passes to the stripping column for recovery of the ethanol. Most bioreactor arrangements will employ a circulation loop to circulate fermentation broth around the bioreactor and the flash zone may provide part of the broth circulation. The simplicity of the flash zone may also permit its use as part of the purification step to provide dilute ethanol to the stripping column column. To operate, the flash zone basically requires only a heat addition equal to the latent heat of vaporization. This heat may be supplied within the flash zone by a reboiler to avoid excessive heating of the liquid broth. Since the flash zone requires only low temperature heat inputs there are numerous opportunities for beneficial heat inputs and heat exchange.

DETAILED DESCRIPTION OF THE INVENTION

This invention may be applied to any bioconversion process that produces an aqueous stream containing a dilute concentration of ethanol. Bioconversions of CO and $H_2/CO_2$ to acetic acid, ethanol and other products are well known. For example, in a recent book concise description of biochemical pathways and energetics of such bioconversions have been summarized by Das, A. and L. G. Ljungdahl, *Electron Transport System in Acetogens* and by Drake, H. L. and K. Kusel, *Diverse Physiologic Potential of Acetogens*, appearing respectively as Chapters 14 and 13 of Biochemistry and Physiology of Anaerobic Bacteria, L. G. Ljungdahl eds, Springer (2003). Any suitable microorganisms that have the ability to convert the syngas components: CO, $H_2$, $CO_2$ individually or in combination with each other or with other components that are typically present in syngas may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385 filed Aug. 31, 2006 entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol. Other suitable microorganisms include *Clostridium Ljungdahli*, with strains having the identifying characteristics of ATCC 49587 (U.S. Pat. No. 5,173,429) and ATCC 55988 and 55989 (U.S. Pat. No. 6,136,577) that will enable the production of ethanol as well as acetic acid. All of these references are incorporated herein in their entirety.

Figure 1:
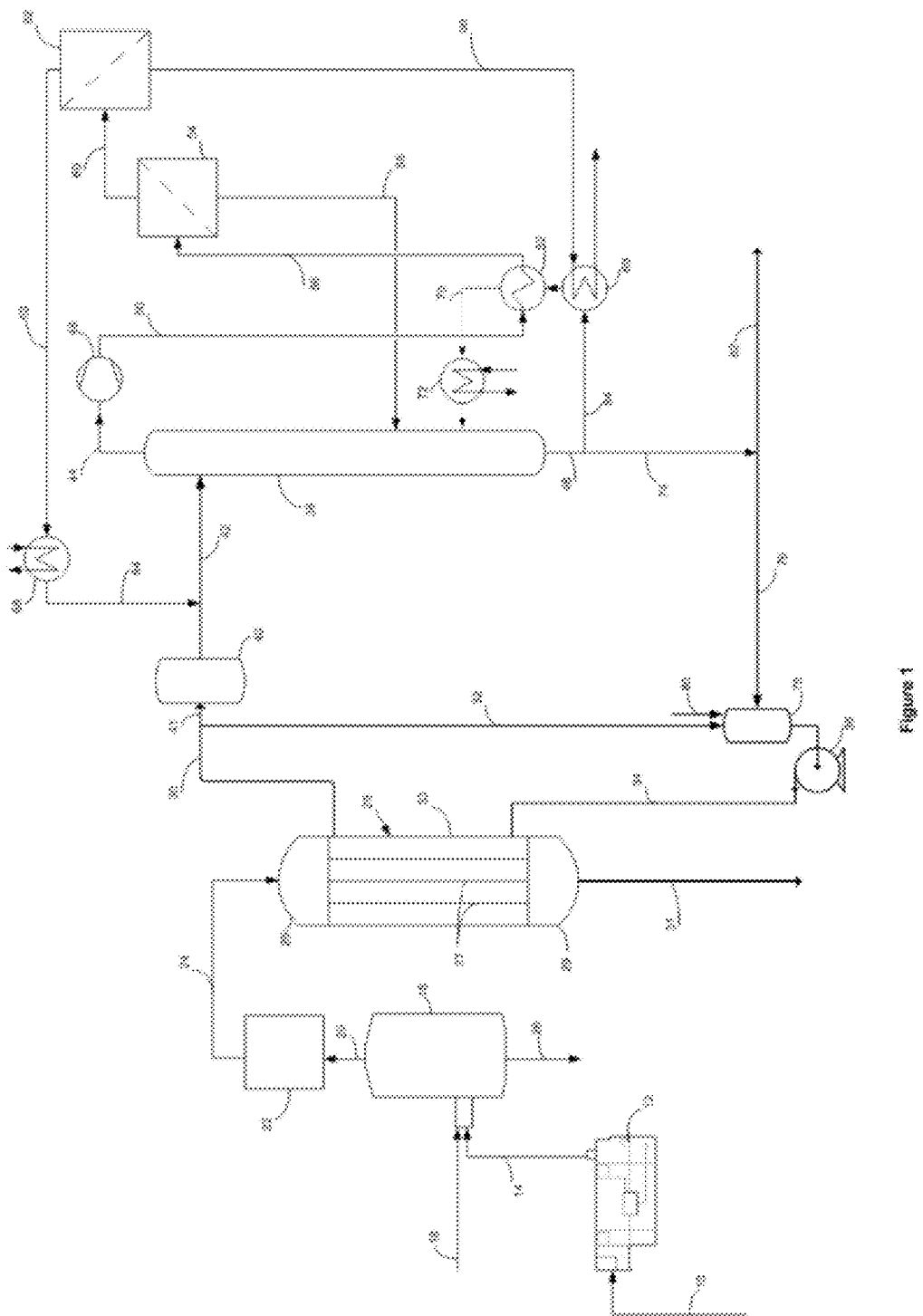
FIG. 1 is a schematic drawing showing the flow arrangement of this invention.

FIG. 1 shows a basic flow schematic for the process and arrangement of this invention. Depiction of the invention in a schematic form does limit the invention to the detail and components shown therein which are provided for purposes of exemplification and not limitation.

Any form of biomass can provide a source of syngas components for use in a bioreactor of this invention. FIG. 1 shows biomass source 10 passing into a dryer 12 and dried biomass 14 conveyed into a gasifier 16 where it contact an oxygen source provided via a line 18. Gasification produces residual ash 26 that leaves the gasifier and a raw syngas stream carried by a line 20. The raw syngas undergoes a series of heat recovery and gas cleaning steps 22 before line 24 carries it to a bioconversion zone in the form of a bioreactor 28.

This invention can integrate many suitable bioconversion zones into the separation system. Suitable bioconversion zones will retain a reservoir of aqueous liquid in a bioreactor. The aqueous liquid, typically a fermentation broth will contain ethanol in a concentration of from 1 to 6 wt % and more narrowly in a range of from 2 to 4 wt % ethanol. Particularly suitable bioreactors retain the microorganisms in the form of a biofilm on a substrate surrounded by a fermentation broth. Such substrates include free floating media as described in U.S. Ser. No. 11/833,864 (filed Aug. 3, 2007) the content of which is hereby incorporated by reference.

The instant invention is particularly suited for bioreactors that use microporous membranes or non-porous membranes or membranes having similar properties to transfer (dissolve) gases into liquids for delivering the components in the syngas directly to the cells that use the CO and $H_2$ in the gas and transform them into ethanol and other soluble products. These membranes concurrently serve as the support upon which the fermenting cells grow as a biofilm and are thus retained in a concentrated layer. Membranes for such applications generally have two important geometries—hollow fiber and flat sheets. These can then be made into modules by appropriate potting and fitting. These modules have very high surface area of pores in small volumes. The result is a highly efficient and economical transfer of the syngas at essentially 100% dissolution and utilization.

In membrane arrangements the syngas diffuses through the membrane from a gas side to a liquid side of the membrane and into a biofilm retained thereon. Microbes transform the syngas into the soluble product of interest. A vessel typically retains the liquid side of the membranes submerged in a fermentation broth. The fermentation broth is passed over the liquid side of the membranes via pumping, stirring or similar means to remove the ethanol and other soluble products formed; the products are recovered via a variety of suitable methods. U.S. Ser. No. 11/781,717 (filed Jul. 23, 2007) shows the use of such a bioreactor and the content of which is hereby incorporated by reference.

FIG. 1 shows the arrangement of this invention incorporating bioreactor 28 as a membrane type bioreactor. Line 24 delivers the feed gas containing CO, $H_2$, and $CO_2$ to a feed gas distribution chamber 25 that distributes the feed gas stream to the lumens of a plurality of tubular membranes elements 27. A collection chamber 29 collects an exhaust gas of unreacted feed gas components that leave the bioreactor 28 via a line 31. During the bioconversion, excess $CO_2$ is generated and this gas can diffuse back and dilute out the concentrations of CO and $H_2$ in the feed gas and thus reduce their mass transfer rates. Suitable systems may be used to reduce CO2 concentrations in the exhaust gas of line 31.

A tank 33 surrounds the outside of the tubular membrane elements 27 in the membrane supported bioreactor and retains a liquid for growth and maintenance of a biofilm layer on the outer surface of the membrane. The tank provides the means of temperature and pH controls for the liquid, which contains nutrients needed to sustain the activity of the microbial cells. The liquid in the tank is stirred to provide adequate mixing and sparged with a suitable gas, if necessary, to maintain a suitable gaseous environment.

In the membrane bioreactor arrangement the feed gas flows continuously or intermittently to a gas chamber of the membrane unit. The feed gas pressure is in the range of 1 to 1000 psia, preferably 5 to 400 psia, and most preferably 10 to 200 psia. Operating at higher gas pressures has the advantage of increasing the solubilities of gases in the liquid and potentially increasing the rates of gas transfer and bioconversion. The differential pressure between the liquid and gas phases is managed in a manner that the membrane integrity is not compromised (e.g., the burst strength of the membrane is not exceeded) and the desired gas-liquid interface phase is maintained. Therefore liquid pressures will generally correspond to the same ranges as those given for the feed gas pressure.

A portion of the fermentation broth is withdrawn from tank 33 of bioreactor 28 via a line 30 to provide the ethanol effluent that is separated into the recycle broth and the dilute ethanol stream for recovery of the ethanol product. This ethanol effluent may be withdrawn from any convenient location of the bioreactor arrangement. The withdrawal rate of ethanol effluent depends on the particular bioreactor arrangement.

Most bioreactor arrangements include a broth circulation and recycle loop from which the broth that contacts the microorganism may be withdrawn to provide the ethanol effluent. FIG. 1 shows a recycle loop consisting of line 30 and lines 32 and 34. A pump 36 maintains circulation of the fermentation broth through the loop. Desired flow conditions within the bioreactor typically dictate the flow rate in the recirculation loop. For example in a membrane bioreactor the recirculation rate is selected so that there is no significant liquid boundary layer that impedes mass transfer near the liquid-facing side of the membrane and there is no excessive shear that may severely limit the attachment of cells and formation of the biofilm on the membrane surface. The superficial linear velocity of the liquid, tangential to the membrane, should be in the range of 0.01 to 20 cm/s, preferably 0.05 to 5 cm/s, and most preferably 0.2 to 1.0 cm/s.

A portion of the ethanol effluent passes to the stripping column 38 via lines 41 and 42 as a dilute ethanol stream and the remainder of it returns as broth fraction to the bioreactor via the recirculation loop. The volume of the dilute ethanol stream withdrawn from the recirculation loop is determined by the desired concentration of ethanol in the fermentation broth. Ethanol must be removed from the fermentation broth to preserve the metabolic processes of the microorganisms by keep the ethanol below a concentration that inhibits their activity. Conversely, the overall efficiency of recover ethanol from the broth improves with higher ethanol concentration. Thus, setting the desired concentration of the ethanol in the fermentation broth requires a balancing of the microorganism at lower ethanol concentrations against improved efficiency of ethanol recovery at higher ethanol concentrations. Depending on the microorganisms, an ethanol concentration of 2 to 4 wt % generally sets the best balance and typically at least 10 wt % of the ethanol effluent enters the distillation column as the dilute ethanol stream.

Before entering the distillation column the dilute ethanol stream may undergo purification in a purification zone 40 for the removal of biological materials and other dissolved matter. The purification zone may use any suitable means such as filtration or ultra-filtration to recover these materials. Microorganisms retained in the purification zone may be returned to the fermentor.

Ordinarily purification zone 40 supplies a liquid phase stream to column 38. This column may function primarily as a stripping column, or may be a conventional distillation column with stripping and rectification sections. The terms stripper or stripping column and distillation column are used interchangeably herein to refer to either type of column. A step-down in pressure vaporizes at least a portion and preferably all of the liquid prior to entering column 38. A pressure regulator (not shown) will supply the step-down in pressure. In preferred form the liquid stream will pass through an expansion valve that vaporizes all of the liquid in line 42.

The distillation column separates the dilute ethanol stream into an overhead vapor stream 44 and an ethanol depleted bottoms stream 46. Dilute ethanol enters near the top stage of the column 38. When operating under vacuum conditions the distillation column will normally operate at a pressure of about 200 torr to 500 torr. Separation requirement of the column will vary with the ethanol concentration of the entering dilute ethanol stream. At higher ethanol concentration the vacuum column will normally provide at least 10 stages of separation. More typically the column will have about 15 stages of separation and will operate in the range of 300 to 400 torr. Ordinarily column in vacuum mode will provide an ethanol concentration of at least 30 wt % a more often at least 40 wt % in the overhead vapor stream. At low concentrations, the vacuum conditions and stages of the separation will permit the column to operate with a relatively low maximum temperature of about 80 C.

The ethanol concentration of the bioreactor effluent in line 42 will also affect the need for any reflux of the vapor stream 44. Typically for ethanol concentrations greater than 3 wt % in line 42, the desired concentration of ethanol in line 44 can be attained without any recycle of the vapor stream 44 directly to the column 38. For lower bioreactor effluent concentration in line 42, suitable condensing and reflux equipment (not shown) may be provided as necessary to achieve the desired concentrations of ethanol in vapor stream 44.

The overhead vapor from the column 38 undergoes compression in compressor 48 and passes via a line 50 through heat exchanger or aftercooler 52 before entering a first vapor permeation unit 54 via a line 56. Compression of the overhead vapor raises its pressure to range of 2 to 4 atmospheres. The compressed overhead vapor passes through heat exchanger 52 to reduce its temperature to about 90 to 110 C. Optionally, heat exchange of the compressed vapor supplies heat to the bottom of the column.

The first vapor permeation unit 54 has a high efficiency vapor permeation membrane that separates the overhead vapor into permeate and retentate streams. Although the Figures schematically show the permeation units as containing one membrane each unit may include a plurality of membranes in parallel or series flow. The permeation membranes may be any suitable material that provides a separation factor in favor of water over ethanol and is substantially insoluble in an organic solvent. Examples of suitable membranes are described in co-owned and co-pending U.S. patent application Ser. Nos. 11/715,245 and 11/897,675, the contents of which are incorporated herein by reference. These membranes include a selective layer of a polymer incorporating repeat units of a fluorinated dioxole or a similar fluorinated ring structure. Other suitable membranes and materials may be those disclosed in US 2006/0117955 A1.

Permeation of a water vapor enriched stream through the membrane produces permeate stream 58 having an ethanol concentration in a range of 2 to 6 wt % and retentate stream 60 having an ethanol concentration of 70 to 90 wt %. The permeate stream returns as a vapor to provide reflux to the middle of the column. The ethanol enriched retentate provides the feed to the next permeation unit 62.

The next vapor permeation unit 62 also has a high efficiency hydrophilic pervaporation membrane that separates the retentate stream 60 into permeate and retentate streams. Vapor permeations unit 62 may use the same membrane as permeation unit 54 or a membrane of any suitable material that provides a separation factor in favor of water over ethanol and is substantially insoluble in an organic solvent. Permeation of a water vapor in unit 62 dehydrates stream 60 to produce a permeate stream 63 with an ethanol concentration in a range of about 10 to 35 wt % and the retentate stream 66 with an ethanol concentration of at least 99 wt %.

The permeate stream 63 contains an ethanol and water vapor. Heat exchanger 68 may provide any desired cooling of permeate in line 64. Typically heat exchanger 68 will fully condense the vapor stream that line 64 returns to the top of column 38. Suitable equipment such as a pump (not shown) in line 64 or compressor (not shown) in line 63 may be provided to maintain the desired pressure differential between vapor permeation unit 60 and column 38. Line 64 returns the permeate via line 42. In some cases (not depicted in FIG. 1) a separate line may deliver the permeate to the column at a point above the dilute ethanol carried by line 42.

Line 66 recovers the dehydrated ethanol stream. All or a portion of this stream may be recovered as an ethanol product.

Heat from the contents of line 66 may be recovered for use in the bottom of the vacuum column 38. An extensive heat integration is effected at the bottom of the vacuum column by withdrawing liquid from line 46 via a line 84 for a reboiler loop wherein the liquid first undergoes heat exchange with the retentate of line 66 in an exchanger 69 and then the liquid passes via line 70 for heat exchange with overhead of line 50 in exchanger 52. Any final adjustment of the heat input for vacuum column 38 is provided by heat exchanger 72.

Line 74 withdraws the net bottoms from vacuum column 38. The majority of the net column bottoms, typically more than 90%, returns to the broth recirculation loop via a line 76 and a mixing chamber 78. A nutrient feed is added via line 80, as needed, to compensate for the amount of water removed from the separation step and to replenish nutrients needed to maintain the activity of the microorganisms. Chamber 78 provides any mixing of the various streams and components before they return to tank 33 via line 18.

A minor portion of the net bottoms are removed as a purge stream via line 82. These bottoms may be sent to a methane digestor to convert the soluble, colloidal and other organic waste to methane for energy recovery and to reduce the waster treatment load from the process.

It has also been found that in certain cases the use of flash zone to provide an initial enrichment of the ethanol feed to the distillation step may improve the efficiency of the separation. The flash provides the most benefit where the ethanol concentration in the ethanol effluent is 2.4 wt % or higher. With the addition of the flash step and suitable heat integration the distillation and dewatering steps of the vapor permeation may units may effectively treat ethanol effluents with ethanol concentrations as low as 1.2 wt %. The flash step is particularly effective when ethanol effluent has an ethanol concentration is in a range of from 2.4 to 4. The flash zone will usually produce an overhead vapor stream having from 5 to 30 wt % ethanol.

When added, the flash zone may eliminate the need for the purification unit. Flashing of the ethanol containing vapor leaves essentially all of the biological materials and other dissolved and undissolved matter contained in the dilute ethanol stream. A small amount of the flash column bottoms stream may be purged as necessary to maintain the dissolved and undissolved matter at desired concentrations.

The flash zone effects an initial separation by releasing pressure on the liquid ethanol to create a vapor phase that is richer in the more volatile ethanol component. The zone will typically include an expansion valve or similar device for discharging in the ethanol effluent into a vessel such as a drum or chamber that provides expansion space to allow the first vapor stream to form. The flash step may be performed adiabatically or non adiabatically.

In one aspect of this invention a small external heater may provide heat input for the flash to the incoming liquid. Such arrangements will normally include a first heat exchange of the incoming dilute ethanol stream with flash column bottoms to recover heat and reduce the external heat input.

In another form of this invention a direct heating of liquid within a vessel provides a non-adiabatic flash. In this form a heated flash vessel maintains a liquid level over heating coils contained therein. The heating of the liquid provides the enthalpy for evaporation at low pressure and the vapor liquid split is controlled by the amount of heat added to the vessel.

The heat requirements of the flash step depend largely on the flashing pressure maintained in the flash zone. To avoid heating of the ethanol effluent from the bioreactor the flash must operate at very low pressure typically less than 60 torr. However, reducing the required size of equipment and providing compatibility with the downstream column favors use of somewhat higher pressures. Heating the ethanol effluent to about 65° C. will bring the required pressure of the flash step up to about 190 torr and heating the effluent to about 80° C. will increase the pressure to about 380 torr. Suitable exchangers can provide heating of the ethanol effluent against the flashed liquid from flash zone as well as any sensible heat input necessary to make up for losses in the heat exchange.

Figure 2:
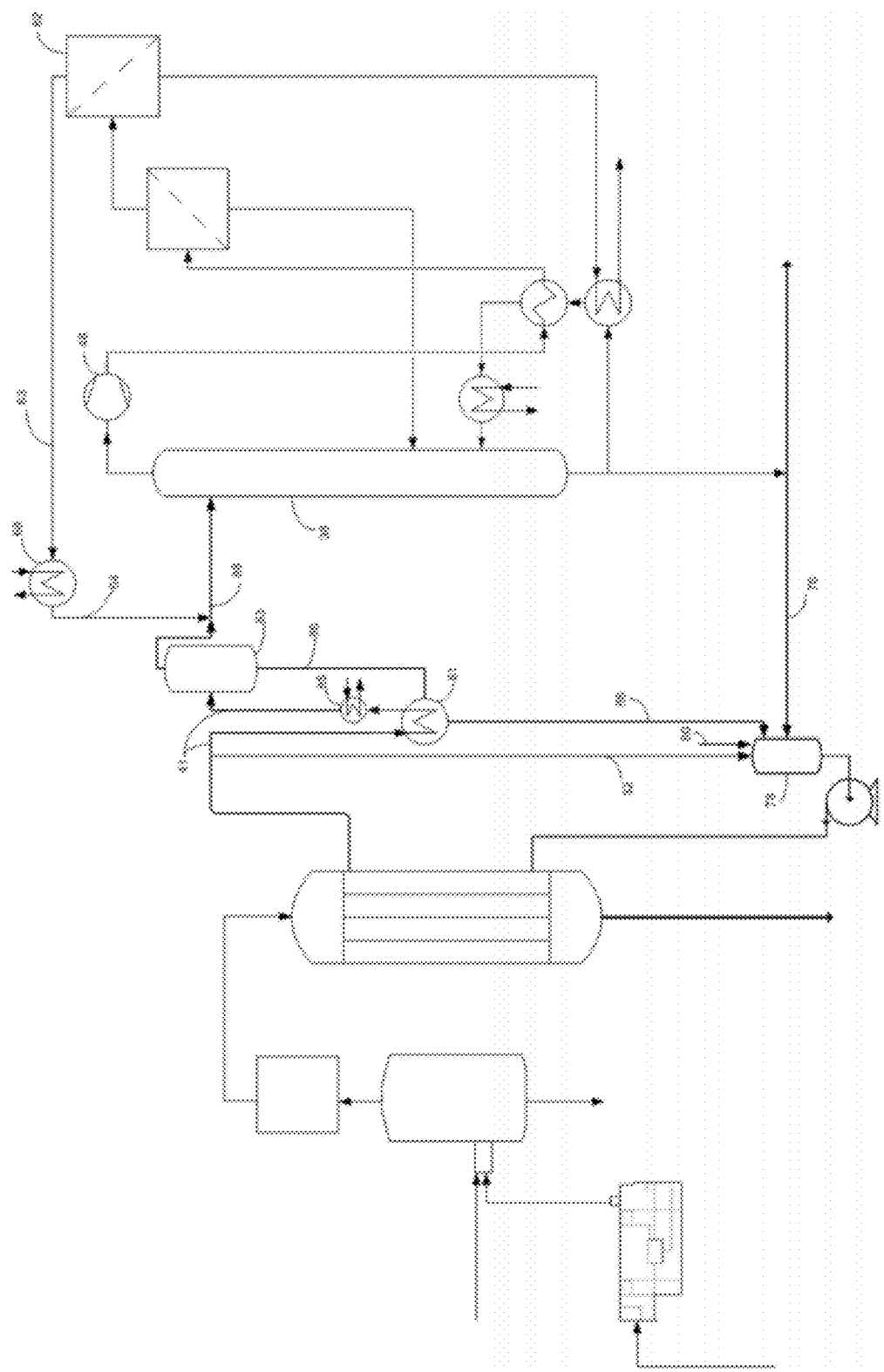
FIG. 2 is a schematic drawing showing the flow arrangement of FIG. 1 modified to include a flash zone.

FIG. 2 shows the arrangement of this invention with the addition of a flash zone. All similar elements of FIG. 2 have the same numbering as FIG. 1.

The flash zone as depicted in FIG. 2 includes a flash vessel 83 that receives the dilute ethanol stream of line 41' without passing it through the purification zone which is now eliminated. A line 86 carries the flash vessel bottoms through an exchanger 81 that raises the temperature of dilute ethanol stream by recovering heat from the bottoms stream 86. The contents of line 41' then pass through heater 85 that provides the net heat input for the flash. Flashing of the vapor leaves any residual solid material in the liquid phase for recovery and return to the recirculation loop of the bioreactor via line 86 and chamber 78. In some arrangements it may be advantageous to heat the incoming dilute ethanol stream by heat exchange with the flash column bottoms stream.

Line 88 carries overhead vapor from the flash to distillation column 38. In this arrangement vapor from the flash vessel 83 enters to the top of the distillation column 38 along with the permeate stream from line 64.

Example 1

For convenience this invention is further described in the context of a calculated example using a membrane type bioreactor. Such description is not intended to limit the separation described herein to the particular arrangement of this example or to any particular bioreactor arrangement. Any bioreactor producing ethanol in a liquid medium may be integrated with the separation elements of this invention.

To establish a conversion level of a typical syngas type feed a Liqui-Cel® membrane contactor MiniModule® 1×5.5 from Membrana (Charlotte, N.C.) is used as a membrane supported bioreactor for the conversion of carbon monoxide and hydrogen into ethanol. This membrane module contains X50 microporous hydrophobic polypropylene hollow fibers with 40% porosity and 0.04 µm pore size. The fiber outer diameter is 300 µm and internal diameter 220 µm. The active membrane surface area of the module is 0.18 m². A gas containing 40% CO, 30% $H_2$, and 30% $CO_2$ is fed to the lumen of the fibers at 60 std ml/min and 2 psig inlet pressure and the residual gas exits the module at 1 psig outlet pressure. The membrane module is connected to a 3-liter BioFlo® 110

Fermentor from New Brunswick Scientific (Edison, N.J.). The fermentation medium having the composition given in Table 2 is pumped from the fermentor, flows through the shell side of the membrane module, and returns to the fermentor. The flow rate of this recirculating medium is 180 ml/min, and the pressure at the outlet of the membrane module is maintained at 5 psig by adjusting a back-pressure valve. The fermentor contains 2 liters of the fermentation medium, which is agitated at 100 rpm and maintained at 37° C. The fermentor is maintained under anaerobic conditions.

The fresh fermentation medium contains the components listed in Tables 1 & 2(a)-(d).

TABLE 1

Fermentation Medium Compositions

| Components | Amount per liter |
|---|---|
| Mineral solution, See Table 2(a) | 25 ml |
| Trace metal solution, See Table 2(b) | 10 ml |
| Vitamins solution, See Table 2(c) | 10 ml |
| Yeast Extract | 0.5 g |
| Adjust pH with NaOH | 6.1 |
| Reducing agent, See Table 2(d) | 2.5 ml |

TABLE 2(a)

Mineral Solution

| Components | Concentration (g/L) |
|---|---|
| NaCl | 80 |
| $NH_4Cl$ | 100 |
| KCl | 10 |
| $KH_2PO_4$ | 10 |
| $MgSO_4 \cdot 7H_2O$ | 20 |
| $CaCl_2 \cdot 2H_2O$ | 4 |

TABLE 2(b)

Trace Metals Solution

| Components | Concentration (g/L) |
|---|---|
| Nitrilotriacetic acid | 2.0 |
| Adjust the pH to 6.0 with KOH | |
| $MnSO_4 \cdot H_2O$ | 1.0 |
| $Fe(NH_4)_2(SO_4)_2 \cdot 6H_2O$ | 0.8 |
| $CoCl_2 \cdot 6H_2O$ | 0.2 |
| $ZnSO_4 \cdot 7H_2O$ | 1.0 |
| $NiCl_2 \cdot 6H_2O$ | 0.2 |
| $Na_2MoO_4 \cdot 2H_2O$ | 0.02 |
| $Na_2SeO_4$ | 0.1 |
| $Na_2WO_4$ | 0.2 |

TABLE 2(c)

Vitamin Solution

| Components | Concentration (mg/L) |
|---|---|
| Pyridoxine•HCl | 10 |
| Thiamine•HCl | 5 |
| Roboflavin | 5 |
| Calcium Pantothenate | 5 |
| Thioctic acid | 5 |
| p-Aminobenzoic acid | 5 |
| Nicotinic acid | 5 |
| Vitamin B12 | 5 |
| Mercaptoethanesulfonic acid | 5 |

TABLE 2(c)-continued

Vitamin Solution

| Components | Concentration (mg/L) |
|---|---|
| Biotin | 2 |
| Folic acid | 2 |

TABLE 2(d)

Reducing Agent

| Components | Concentration (g/L) |
|---|---|
| Cysteine (free base) | 40 |
| $Na_2S \cdot 9H_2O$ | 40 |

Initially, the bioreactor system is operated in the batch mode and inoculated with 200 ml of an active culture of *Clostridium ragsdalei* ATCC No. BAA-622. The fermentation pH is controlled at pH 5.9 in the first 24 hours by addition of 1 N $NaHCO_3$ to favor cell growth and then allowed to drop without control until it reaches pH 4.5 to favor ethanol production. After initial operation in the batch mode to establish the attachment of the microbial cells on the membrane surface, the system is switched to continuous operation, with continuous withdrawal of the fermentation broth for product recovery and replenish of fresh medium. After 20 days of continuous operation, the ethanol concentration increases to 10 g/L with the broth withdrawal rate at 20 ml/hr.

Example 2

The conversion rate and flow rates of Example 1 were scaled up to provide input for a calculated example demonstrating the separation of a dilute ethanol stream in the separation section of the process. In accordance with the separation section depicted in FIG. 1, 1136 kg/hr of an ethanol effluent having an ethanol concentration of 1 wt % flows through a purifier while the remaining 22710 kg/hr of an ethanol effluent enters a recirculation loop for its return to the bioreactor as a broth fraction.

The dilute ethanol from the purifier flows into an upper section of a distillation column at a temperature of 76° C. and under vacuum conditions. The vacuum distillation column of this example provides 20 stages of separation. Overhead vapor having an ethanol concentration of 52.5 wt % flows from the vacuum column at a rate of 25.1 kg/hr and a temperature of 73° C. Compression of the vapor to 1.6 atm raises its temperature to 177° C.

Cooling of the vapor in the vacuum column reboiler loop lowers its temperature to 104° C. before it contacts a pervaporation membrane in a first vapor permeation unit. Permeate having an ethanol concentration of 4.6 wt % flows back at a midpoint of the vacuum column at a rate of 8.21 kg/hr, a temperature of 103° C., and a pressure of 0.5 atm.

Retentate with an ethanol concentration of 75.8 wt % flows from the first permeation into contact with a pervaporation membrane in a second vapor permeation unit, at a rate of 16.9 kg/hr, a pressure of 1.6 atm, and a temperature 102° C. The second vapor permeation unit produces a 5.6 kg/hr of permeate having an ethanol concentration of 28.3 wt % and a pressure of 0.1 atm. A condenser cools the second permeate to a liquid by cooling it from 101° C. to 32° C. The condensed liquid passes through a pump that discharges all of condensed permeate at a pressure of 0.5 atm into the top of the vacuum column along with the dilute ethanol from the purifier. Product retentate having an ethanol concentration of 99.43 wt % ethanol flows from the second vapor permeation unit at rate of 11.3 kg/hr for recovery as ethanol product.

The product retentate also provides heat to the reboiler loop of the vacuum column. The reboiler loop takes 9410 kg/hr of the total column bottoms at temperature of 81.5° C. and passes it first in heat exchange with the product retentate and then in heat exchange with the compressed vapor stream from the column. The heated bottoms reenter the column at a temperature 81.5° C.

Net bottoms leave the vacuum column with an ethanol concentration of 0.013 wt %. 1011 kg/hr of the net column bottoms flow back to the bioreactor in admixture with the recirculating broth fraction. Another 112 kg/hr of the net bottoms leave the system as purge.

The invention claimed is:

1. A process for producing ethanol comprising:
    a) contacting a feed gas containing at least one of carbon monoxide or a mixture of carbon dioxide and hydrogen with a microorganism in a bioreactor to metabolize said feed gas and produce an ethanol effluent comprising dilute ethanol having an ethanol concentration of from 1 to 6 wt %;
    b) separating the ethanol effluent into a broth fraction and a dilute ethanol stream;
    c) passing the dilute ethanol stream to a stripping column and recovering an ethanol depleted bottoms stream and an overhead vapor stream enriched in ethanol from the stripping column;
    d) passing at least a portion of the ethanol depleted bottoms stream and at least a portion of the broth fraction to the bioreactor;
    e) compressing the overhead vapor stream to at least 2 atmospheres to produce a compressed vapor;
    f) contacting at least a portion of the compressed vapor stream in a first vapor permeation unit with a membrane to produce a retentate having at least 70 wt % ethanol and a first permeate stream;
    g) returning at least a portion of the first permeate stream to the stripping column;
    h) contacting the retentate in a second vapor permeation unit with a membrane to produce a dehydrated ethanol stream having at least 99.0 wt % alcohol and a second permeate stream;
    i) returning at least a portion of the second permeate stream to the stripping column; and,
    j) recovering at least a portion of the dehydrated ethanol stream as an ethanol product.

2. The process of claim 1, wherein the ethanol depleted bottoms stream comprises acetic acid and the microorganism produces ethanol from acetic acid.

3. The process of claim 2, wherein the ethanol depleted bottoms stream comprises butyric acid and the microorganism produces butanol from butyric acid.

4. The process of claim 1, wherein at least a portion of the dilute ethanol effluent passes to a flash zone to produce a flash bottom stream and an ethanol enriched vapor stream and at least a portion of the ethanol enriched vapor stream passes to the stripping column to provide at least a portion of the dilute ethanol effluent stream to the stripping column.

5. The process of claim 4, wherein the ethanol enriched vapor stream comprises from 5 to 30 wt % ethanol.

6. The process of claim 4, wherein at least a portion of the flash bottom stream passes to the bioreactor.

7. The process of claim 6, wherein at least a portion of the flash bottom stream, and at least a portion of the ethanol depleted bottoms stream return to the bioreactor in admixture with the broth fraction.

8. The process of claim 1, wherein at least a portion of the dehydrated ethanol stream heats the bottoms of the stripping column.

9. The process of claim 1, wherein the dilute ethanol stream comprises at least 10 wt % of the ethanol effluent and has a concentration of from 2 to 4 wt % ethanol.

10. The process of claim 1, wherein a portion of the second permeate stream passes to an anaerobic digester for the production of methane.

11. The process of claim 1, wherein the ethanol effluent has an ethanol concentration greater than 3 wt % and essentially all of the overhead vapor stream from the stripping column passes to the first vapor permeation zone without reflux to the stripping column.

12. A process for producing ethanol comprising:
    a) contacting a feed gas containing at least one of carbon monoxide or a mixture of carbon dioxide and hydrogen with a microorganism in a bioreactor to metabolize said feed gas and produce an ethanol effluent comprising dilute ethanol having an ethanol concentration of from 1 to 6 wt %;
    b) passing at least a portion of the ethanol effluent stream to a flash column to produce a flash bottom stream and an ethanol enriched vapor stream;
    c) passing at least a portion of the ethanol enriched vapor stream to a stripping column and recovering an ethanol depleted bottoms stream and an overhead vapor stream containing at least 30 wt % ethanol from the stripping column;
    d) passing at least a portion of the ethanol depleted bottoms stream and at least a portion of the flash bottom stream to the bioreactor;
    e) compressing the overhead vapor stream to at least 2 atmospheres and indirectly heat exchanging at least a portion of the compressed vapor stream with the bottoms of the stripping column to heat the stripping column and to provide a cooled vapor stream;
    f) contacting the cooled vapor stream in a first vapor permeation unit with a membrane to produce a retentate having at least 70 wt % ethanol and a first permeate stream;
    g) returning at least a portion of the first vapor permeate stream to the stripping column;
    h) contacting the retentate in a second vapor permeation unit with a membrane to produce a dehydrated ethanol stream having at least 99.0 wt % alcohol and a second permeate stream;
    i) returning at least a portion of the second permeate stream to the flash column; and,
    j) recovering at least a portion of the dehydrated ethanol stream as an ethanol product.

13. The process of claim 12, wherein the bottoms stream comprises acetic acid and the microorganism produces ethanol from acetic acid.

14. The process of claim 13, wherein the ethanol depleted bottoms stream comprises butyric acid and the microorganism produces butanol from butyric acid.

15. The process of claim 14, wherein the ethanol enriched vapor stream comprises from 5 to 30 wt % ethanol.

16. The process of claim 15, wherein the ethanol effluent has a concentration of from 2 to 4 wt % ethanol and 10 to 90 vol % of the ethanol effluent passes to the flash column and the remainder is recycled to the bioreactor as a broth fraction.

17. The process of claim 16, wherein the ethanol depleted bottoms stream, the flash bottom stream and the broth fraction are combined in a mixing chamber and returned to the bioreactor.

18. The process of claim 12, wherein the ethanol enriched vapor stream undergoes purification for removal of bio-waste before entering the stripping column.

19. A process for producing ethanol comprising:
a) contacting a feed gas containing at least one of carbon monoxide or a mixture of carbon dioxide and hydrogen with a microorganism in a bioreactor to metabolize said feed gas and produce an ethanol effluent comprising dilute ethanol having an ethanol concentration of from 1 to 6 wt %;
b) passing a portion of the ethanol effluent as a broth fraction to the bioreactor and passing a portion of the ethanol effluent stream to a flash column to produce a flash bottom stream and an ethanol enriched vapor stream;
c) removing bio-waste from at least a portion of the ethanol enriched vapor stream and passing it to an upper location of a vacuum stripping column and recovering an ethanol depleted bottoms stream and an overhead vapor stream containing at least 40 wt % ethanol from the vacuum stripping column;
d) passing at least a portion of the ethanol depleted bottoms stream and at least a portion of the flash bottom stream to the bioreactor;
e) compressing the overhead vapor stream to at least 2 atmospheres and indirectly heat exchanging at least a portion of the compressed vapor stream with the bottoms of the vacuum stripping column to heat the stripping column and to provide a cooled vapor stream;
f) contacting the cooled vapor stream in a first vapor permeation unit with a membrane to produce a first permeate stream with an ethanol concentration of at least 4% and a retentate having at least 90 wt % ethanol;
g) returning at least a portion of the first vapor permeate stream to the vacuum stripping column;
h) contacting the retentate in a second vapor permeation unit with a membrane to produce a dehydrated ethanol stream having at least 99.0 wt % alcohol and a second permeate stream;
i) returning at least a portion of the second permeate stream to the flash column; and,
j) recovering at least a portion of the dehydrated ethanol stream as an ethanol product.

20. The process of claim 19, wherein the ethanol depleted bottoms stream, the flash bottom stream and the broth fraction are combined in a mixing chamber and returned to the bioreactor.

* * * * *